US012618740B2

(12) United States Patent
Stoll

(10) Patent No.: US 12,618,740 B2
(45) Date of Patent: May 5, 2026

(54) MEASURING ARRANGEMENT FOR GAS MONITORING FOR AN ENERGY STORAGE OF A MOTOR VEHICLE, ENERGY STORAGE ARRANGEMENT FOR A MOTOR VEHICLE AND METHOD FOR OPERATING A MEASURING ARRANGEMENT

(71) Applicant: AUDI AG, Ingolstadt (DE)

(72) Inventor: Simon Stoll, Manching (DE)

(73) Assignee: AUDI AG, Ingolstadt (DE)

( * ) Notice: Subject to any disclaimer, the term of this patent is extended or adjusted under 35 U.S.C. 154(b) by 376 days.

(21) Appl. No.: 18/499,269

(22) Filed: Nov. 1, 2023

(65) Prior Publication Data

US 2024/0151606 A1     May 9, 2024

(30) Foreign Application Priority Data

Nov. 9, 2022     (DE) .......................... 102022129662.8

(51) Int. Cl.
| | |
|---|---|
| *G01M 3/04* | (2006.01) |
| *B60L 58/10* | (2019.01) |
| *G01K 3/00* | (2006.01) |
| *G01R 31/3842* | (2019.01) |
| *H01M 10/48* | (2006.01) |

(Continued)

(52) U.S. Cl.
CPC .............. *G01M 3/04* (2013.01); *B60L 58/10* (2019.02); *G01K 3/005* (2013.01); *G01R 31/3842* (2019.01); *H01M 10/486* (2013.01); *B60L 3/0046* (2013.01); *G01N 33/0004* (2013.01); *H01M 2220/20* (2013.01)

(58) Field of Classification Search
CPC ........ G01M 3/04; B60L 58/10; B60L 3/0046; G01K 3/005; G01R 31/3842; H01M 10/486; H01M 10/42; H01M 10/4228; H01M 10/48; H01M 2220/20; H01M 2220/00; G01N 33/0004
See application file for complete search history.

(56) References Cited

U.S. PATENT DOCUMENTS

2021/0190881 A1 *  6/2021  Lee ..................... H01M 10/633
2024/0063444 A1 *  2/2024  Jemison .............. H01M 10/486

FOREIGN PATENT DOCUMENTS

CN       111391668 A  *  7/2020  ............ B60L 3/0046
CN       111799248 A     10/2020

(Continued)

OTHER PUBLICATIONS

CN111799248A English Translation (Year: 2020).*
Search Report issued on Sep. 28, 2023, in corresponding German Application No. 102022129662.8, 16 pages.

*Primary Examiner* — Jonathan M Dunlap
(74) *Attorney, Agent, or Firm* — Maier & Maier, PLLC

(57)     ABSTRACT

A measuring arrangement for gas monitoring for an energy storage of a motor vehicle, which includes at least one battery cell. The measuring arrangement has a gas sensor unit which includes at least one first sensor. The gas sensor unit is designed to detect a gas leak from the at least one battery cell. In particular, the measuring arrangement is designed in such a way that at least in a first operating state of the gas sensor unit, at least the first sensor can be woken up from an inactive idle state for carrying out at least one measurement and can be put back into the inactive idle state after the at least one measurement has been carried out.

15 Claims, 2 Drawing Sheets

(51) Int. Cl.
*B60L 3/00* (2019.01)
*G01N 33/00* (2006.01)

(56) References Cited

FOREIGN PATENT DOCUMENTS

| | | | | | |
|---|---|---|---|---|---|
| CN | 111942216 | A | * | 11/2020 | ................ B60L 3/00 |
| CN | 111942217 | A | * | 11/2020 | .............. B60L 58/10 |
| CN | 113571782 | A | * | 10/2021 | ............. G01D 21/02 |
| CN | 115207577 | A | | 10/2022 | |
| CN | 120184475 | A | * | 6/2025 | ........... H01M 10/48 |
| DE | 102013206922 | A1 | | 5/2014 | |
| DE | 102015115695 | A1 | | 3/2017 | |
| DE | 102020102561 | B3 | | 5/2021 | |
| DE | 102020109544 | A1 | | 10/2021 | |
| DE | 102020005167 | A1 | | 2/2022 | |
| DE | 102021102049 | A1 | * | 8/2022 | ........... H01M 10/48 |

* cited by examiner

MEASURING ARRANGEMENT FOR GAS MONITORING FOR AN ENERGY STORAGE OF A MOTOR VEHICLE, ENERGY STORAGE ARRANGEMENT FOR A MOTOR VEHICLE AND METHOD FOR OPERATING A MEASURING ARRANGEMENT

FIELD

The invention relates to a measuring arrangement for gas monitoring for an energy storage of a motor vehicle, which comprises at least one battery cell, wherein the measuring arrangement has a gas sensor unit which comprises at least one first sensor, wherein the gas sensor unit is designed to detect a gas leak from the at least one battery cell. Furthermore, the invention also relates to an energy storage arrangement for a motor vehicle and a method for operating a measuring arrangement.

BACKGROUND

Such a gas sensor unit, which is also sometimes referred to as a gas sensor or thermal runaway sensor, can be used in an energy storage to detect a thermal runaway, namely an uncontrolled thermal runaway, or the beginning of such a thermal runaway of one or more battery cells. In particular, a gas leak from the battery cell can be detected using such a sensor. If gas leaks from the battery or a battery cell, a fire is very likely to occur. This advantageously makes it possible to initiate countermeasures at an early stage, in particular before such a fire has developed.

A traction battery with a gas sensor is also described, for example, in DE 10 2020 102 561 B3.

In principle, a thermal runaway of a battery cell can occur at any time, namely not only when driving, but also when the motor vehicle is inactive, for example at night and/or during a charging process. Accordingly, such gas sensors for gas monitoring in the energy storage are kept in continuous operation, whereby the gas sensor is permanently switched on and also continuously carries out measurements. This means that any gas leakage from a battery cell can be detected at any time. On the other hand, however, this leads to very high power consumption and the overall service life of the gas sensor is also severely limited.

Furthermore, it is known from DE 10 2015 115 695 A1 that a device in a motor vehicle can be operated in a so-called wake mode, in which it is fully functional, and can be operated in a sleep mode, which is also called stand-by mode and in which the device is operated with a sleep current that is lower than the wake current. If the device is operated by a user, this operation of the device should also be recognized by the device in sleep mode in order to be able to switch back to wake mode.

However, the functionality of a gas sensor for gas monitoring in an energy storage is not only required every now and then, but permanently in order to be able to detect a gas leak from a battery cell at any time.

SUMMARY

The object of the present invention is therefore to provide a measuring arrangement, an energy storage arrangement and a method which allow the most energy-efficient but at the same time safe operation of a gas sensor unit.

A measuring arrangement according to the invention for gas monitoring for an energy storage of a motor vehicle, which comprises at least one battery cell, has a gas sensor unit which comprises at least one first sensor, wherein the gas sensor unit is designed to detect a gas leak from the at least one battery cell. The measuring arrangement is designed in such a way that at least in a first operating state of the gas sensor unit, at least the first sensor can be woken up from an inactive idle state for carrying out at least one measurement and can be put back into the inactive idle state after the at least one measurement has been carried out.

The invention is based on the knowledge that there can be longer periods of time, in particular several minutes or more, between a gas leak from a battery cell and the occurrence of a battery fire. In order to detect a gas leak in a timely manner and to be able to initiate a countermeasure before the fire occurs, it is not necessary to carry out high-frequency, quasi-permanent gas monitoring. Accordingly, it is sufficient, for example, to wake up the at least one sensor from an idle state every now and then to carry out a measurement, for example every few minutes or if, based on other sensor measurements, of which a large number are typically carried out in an energy storage, in particular also using other sensors, there is a suspicion that gas could be leaking or is leaking from a battery cell. This advantageously makes it possible to save enormous amounts of energy, since the first sensor of the gas sensor unit does not have to be permanently active and constantly carry out measurements. Nevertheless, security is not compromised. In addition, the service life of the gas sensor unit can also be increased.

If, for example, abnormalities are detected during gas monitoring, the gas sensor unit can also be transferred to a second operating state, in which measurements are then carried out, for example, more frequently or permanently using the first sensor. In principle, in addition to the first operating state, a second operating state can also be provided, in which the gas sensor unit is in continuous operation or in the permanent wake state, and accordingly continuously carries out measurements for gas monitoring. The first operating state, in which at least the first sensor of the gas sensor unit or the gas sensor unit as a whole is at least temporarily in a idle state and is woken up to carry out a measurement, can also be the only operating state in which the gas sensor unit can be operated.

The motor vehicle's energy storage is preferably a high-voltage battery. Incidentally, this can include not just one battery cell, but preferably a large number of battery cells. These battery cells can be formed, for example, as lithium-ion cells. For gas monitoring, one gas sensor unit for the entire energy storage is then sufficient. Nevertheless, it is conceivable that several such gas sensor units are provided in or on an energy storage. The gas sensor unit is preferably arranged in an interior of the energy storage, that is to say in a battery housing of the energy storage. This allows gas monitoring to be provided in the energy storage, namely within the battery housing. The gas sensor unit can, for example, monitor the gas composition of the gas present inside the energy storage, usually air, and in the event of changes, for example in case of an increase in a certain gas proportion, for example $H_2$ (hydrogen), and/or ammonia and/or CO (carbon monoxide) and/or $CO_2$ (carbon dioxide), it can detect a possible gas leak or generally a thermal runaway of the at least one battery cell. A gas exiting the at least one battery cell can thus come into contact with the gas sensor unit. In principle, however, it is also conceivable to arrange the gas sensor unit elsewhere. For example, the unit can also be arranged within a gas discharge channel for discharging gases emerging from the at least one battery cell from the energy storage and in particular from the motor vehicle. It is therefore also conceivable that the gas sensor unit is located in a part of such a gas discharge channel that is arranged outside the battery housing.

In principle, the gas sensor unit can include not only the first sensor, but also a second sensor, a third sensor and so on. The gas sensor unit preferably has several, in particular different, sensors, as these will be explained in more detail later. It is precisely by combining these measurement signals sensed by the various sensors that a gas leak from a battery cell can be reliably detected. The sensors of the gas sensor unit are preferably arranged in a common sensor housing. In other words, it is preferred that a structural unit is provided by the gas sensor unit. The sensors belonging to the gas sensor unit should therefore not be arranged in any spatially distributed manner in or on the energy storage, but rather positioned, as described, housing and therefore at approximately the same position within the energy storage. As a result, the different measured variables detected by the individual sensors of the gas sensor unit can be reliably correlated to one another.

The inactive idle state of the gas sensor unit can be designed such that the gas sensor unit requires less power in this inactive idle state than in the active state or in the wake state, in which at least the first sensor carries out a measurement. It may also be the case that the gas sensor unit does not require any power at all in the inactive idle state. Alternatively, the gas sensor unit can be operated in the idle state with a non-zero idle current. In addition, the inactive idle state of the gas sensor unit can be defined such that no measurements are carried out by the at least one first sensor of the gas sensor unit in this inactive idle state. The inactive idle state, in which no measurements are carried out by the first sensor, can be a first inactive idle state. If the gas sensor unit has several sensors, either a common idle state can be defined for all of them or a separate idle state can be defined for each sensor, such as a second idle state for a second sensor, in which the second sensor does not carry out any measurements and is operated with an idle current that is reduced compared to an active state, even to zero, while, for example, the first sensor can still carry out a measurement in the second idle state.

It can also be provided that the gas sensor unit or the at least one sensor is woken up from the inactive idle state not just once, but several times. The time interval between two wake-up times can be several seconds, in particular at least one minute and preferably even several minutes. If the first sensor is woken up to carry out a measurement, it can either carry out a single measurement or several consecutive measurements during the wake-up phase before it is returned to the inactive idle state again.

In a further advantageous embodiment of the invention, the measuring arrangement is designed such that at least the first sensor is woken up repeatedly in the first operating state of the gas sensor unit, in particular at predetermined first time intervals, in order to carry out a measurement. The respective first time intervals can be of different lengths or can be the same. This enables a particularly simple implementation. The at least one first sensor can be woken up by an external control unit or the gas sensor unit itself can be designed such that it activates the first sensor at repeated time intervals in order to carry out at least one measurement. This advantageously makes it possible to provide regular monitoring of the gas composition inside the energy storage.

As already mentioned, the predetermined first time intervals can be several seconds and in particular at least one minute and preferably several minute in length. Furthermore, it is preferred that the first time intervals are at most in the single-digit minute range. This means that a timely countermeasure can still be taken if, during a measurement, a gas escaping from a battery cell is detected or if it is detected that gas is escaping from the at least one battery cell.

In a further advantageous embodiment of the invention, the measuring arrangement is designed such that at least the first sensor is woken up to carry out the measurement in the first operating state of the gas sensor unit as a function of a wake-up signal. This allows particularly good adaptation to the situation. The wake-up signal can be provided, for example, if there is a specific indication of a possible leakage of gas from the battery cell or an indication of a possible thermal runaway of the at least one battery cell. The gas sensor unit can be designed accordingly to detect such a wake-up signal and, depending on the detection of such a wake-up signal, to transfer the first sensor into the active state in order to carry out a measurement using this first sensor. This can also apply in the same way to all other optional sensors included in the gas sensor unit.

In a further advantageous embodiment of the invention, the measuring arrangement has a control device which is designed to wake up at least the first sensor in the first operating state of the gas sensor unit, in particular to provide the wake-up signal depending on the detection of a specific event, in particular wherein the specific event represents a predetermined temperature increase detected by a temperature sensor of the measuring arrangement, and/or an exceeding of a predetermined limit temperature detected by means of a temperature sensor of the measuring arrangement, and/or an accident detected by means of a crash sensor of the measuring arrangement, and/or a specific characteristic determined by means of a current and/or a voltage sensor, of an electrical current or an electrical voltage of the at least one battery cell and/or of the energy storage.

The sensors mentioned can also be part of the measuring arrangement. Typically, several temperature sensors are provided in an energy storage. The gas sensor unit can also have such a temperature sensor, as explained in more detail later, wherein the cited temperature sensors should not be viewed as part of the gas sensor unit. In other words, these can be temperature sensors in the energy storage, by means of which permanent temperature monitoring can be provided, even if the gas sensor unit is in the inactive idle state. If there are abnormalities in the detected temperature, this can represent the specific event, depending on which the wake-up signal for waking up at least the first sensor of the gas sensor unit is provided and through which the first sensor is also woken up accordingly. A predetermined temperature increase can, for example, represent a temperature increase with a specific time gradient that exceeds a predetermined threshold value. Exceeding a predetermined limit temperature by the temperature detected by the at least one temperature sensor can also serve as such a trigger event in order to send the wake-up signal to the gas sensor unit or its first sensor. The detection of a crash by a crash sensor can also represent such a triggering event, as can a specific current or voltage abnormality in a detected electrical current or in a detected electrical voltage. This can relate to a cell voltage of the at least one battery cell or a cell current of the at least one battery cell or also to a total voltage or a total current of the energy storage. Such a characteristic can, for example, be in turn the exceeding of a specific time gradient or a predetermined threshold value. Falling below a certain threshold value, especially in the case of cell voltage, can also be conceivably defined as such a characteristic.

In this way, it can advantageously be achieved that the first sensor of the gas sensor unit is only woken up and carries out a measurement if there is reason to assume that a thermal event in a battery cell is imminent or has only recently begun.

In a further advantageous embodiment of the invention, the gas sensor unit has multiple different sensors comprising the first sensor, in particular which are designed to detect at least one of the following events and/or variables: an occurrence of carbon oxide, for example carbon monoxide and/or carbon dioxide, and/or a concentration of carbon oxide, an occurrence of hydrogen and/or a concentration of hydrogen, an occurrence of ammonia and/or a concentration of ammonia, a temperature and/or a gas pressure. The gas sensor unit preferably includes at least three different sensors. This allows gas leakage from a cell to be detected particularly reliably. The gas sensor unit can also have four or five sensors. This allows all of the events and variables mentioned to be detected. For example, a first sensor can be provided which is designed to detect a carbon oxide and/or to determine a concentration of such a carbon oxide. A second sensor can be designed to detect hydrogen, namely H2, and/or to determine a concentration of hydrogen. A third sensor can be designed to detect the occurrence of ammonia and/or to determine a concentration of ammonia. A fourth sensor can be designed as a temperature sensor for detecting a current temperature and a fifth sensor can be designed as a gas pressure sensor for detecting a current gas pressure.

The variables mentioned can also be recorded over time. For this purpose, repeated measurements can be carried out in a wake-up phase. This also makes it possible, for example, to determine whether a significant increase in a carbon oxide concentration or hydrogen concentration or ammonia concentration occurs within a short period of time. Also a brief significant increase in temperature and/or gas pressure can be detected accordingly. In order to reliably detect the gas escape from a battery cell and in particular the beginning of thermal runaway of this battery cell using the gas sensor unit, it is also advantageous to link several of the events and/or variables mentioned with one another. If, for example, based on the detected variables, it is detected that a gas leak from the at least one battery cell is currently taking place with a very high degree of certainty, the measuring arrangement can output a signal to trigger a countermeasure. Such a countermeasure can, for example, consist of activating a cooling device for cooling the energy storage and/or increasing a cooling capacity of the cooling device for cooling the energy storage, and/or of initiating an extinguishing measure, of sending an emergency call, of issuing a warning message to a driver, to trigger an entry in an error memory, or something similar.

In a further advantageous embodiment of the invention, the measuring arrangement is designed such that, at least in the first operating state of the gas sensor unit, all of the sensors included therein can be woken up from an inactive idle state for carrying out at least one respective measurement and can be returned to the inactive idle state after the respective at least one measurement has been carried out. This waking up and transferring back into the idle state can be done for all sensors of the gas sensor unit at the same time, but this does not necessarily have to be the case. When all sensors are woken up at the same time, the entire gas sensor unit is woken up, in a manner of speaking. In other words, the measuring arrangement can also be designed in such a way that, at least in the first operating state, the entire gas sensor unit can be woken up from an inactive idle state in order to carry out a measurement using its respective sensors and can be returned into the idle state after the at least one measurement has been carried out. Waking up can therefore relate to the gas sensor unit as a whole as well as selectively or individually to its individual sensors.

In a further advantageous embodiment of the invention, the measuring arrangement is designed such that, at least in the first operating state of the gas sensor unit, all of the sensors included therein can be woken up from an inactive idle state according to different, predetermined criteria and/or independently of one another in order to carry out at least one respective measurement. In other words, different criteria can be set to wake up the respective sensors. The sensors can still be woken up in a correlated manner, but also independently of one another. For example, it can be provided that initially only a first sensor of the gas sensor unit is regularly woken up to carry out a measurement. Only when this first sensor detects an abnormality can one or more additional sensors of the gas sensor unit be woken up, for example, in order to also carry out a measurement. It can also be provided that a sensor of the gas sensor unit is woken up at regular intervals in order to carry out a measurement, while another sensor of the gas sensor unit is woken up in an event-triggered manner, that is, depending on, for example, a specific detected event.

The wake-up scenarios and wake-up criteria or trigger events and wake-up according to a regular wake-up cycle described above can be combined and implemented in any suitable way for the various sensors of the gas sensor unit.

This allows particularly good adaptation to the situation. In addition, certain abnormalities can be specifically monitored using a suitable factor, for example a specific sensor can be woken up and activated much more frequently when an abnormality is detected.

In a further advantageous embodiment of the invention, the measuring arrangement is designed such that at least a second sensor among the plurality of sensors is woken up repeatedly in the second operating state of the gas sensor unit, at predetermined second time intervals, in order to carry out a measurement. The second time intervals are different from the first time intervals and/or the first and second sensor are woken up at least partially with a time offset, wherein the second time intervals can also be equal to the first time intervals.

For example, the first sensor can be woken up once every minute, and the second sensor every five minutes. It is also conceivable that the sensors are woken up at the same time intervals, but at a different time from one another. Another possibility is to wake up the individual sensors of the gas sensor unit at different time intervals and also offset from one another. Precisely the temporally offset measurement makes it possible to save enormous amounts of energy while still providing quasi-continuous monitoring. For example, a measurement can be carried out by a different sensor every minute. This means that the time intervals between two measurements of the same sensor are several minutes long, which is very energy-saving, and yet minute-by-minute monitoring can be provided.

Accordingly, it is also advantageous if the first and second sensors are woken up at least partially with a time offset from one another. This means that at least temporarily the first sensor carries out a measurement when the second sensor does not carry out a measurement or is in the idle state and/or the second sensor carries out a measurement while the first sensor is in the idle state. At times, measurements can still be simultaneously carried out by the first and second sensor.

Furthermore, the invention also relates to an energy storage arrangement for a motor vehicle having an energy storage and a measuring arrangement according to the invention or one of their embodiments. The advantages mentioned for the measuring arrangement according to the invention and its embodiments thus apply similarly to the energy storage arrangement according to the invention. The energy storage can also be designed as already described above. In particular, the energy storage is preferably a high-voltage battery. This can include a battery housing with battery cells accommodated therein. The gas sensor unit is preferably also arranged in the battery housing. Parts of the measuring arrangement can also be arranged outside the battery housing, for example the control device for controlling or waking up the gas sensor unit. Furthermore, the gas sensor unit can be connected to a BUS system of the motor vehicle. The BUS system is preferably a CAN BUS. The wake-up signal for waking up the gas sensor unit or at least one of its sensors can also be provided via the BUS system.

Furthermore, the invention also relates to a motor vehicle with an energy storage arrangement according to the invention or one of its embodiments or with a measuring arrangement according to the invention or one of its embodiments.

The invention also relates to a method for operating a measuring arrangement for gas monitoring for an energy storage of a motor vehicle, which comprises at least one battery cell, wherein the measuring arrangement has a gas sensor unit which comprises at least one first sensor, wherein the gas sensor unit is designed to detect a gas leak from the at least one battery cell. In particular, in a first operating state of the gas sensor unit, at least the first sensor is woken up from an inactive idle state for carrying out at least one measurement and is put back into the inactive idle state after the at least one measurement has been carried out.

The advantages mentioned for the measuring arrangement according to the invention and its embodiments thus also apply similarly to the method according to the invention.

The control device for the motor vehicle also belongs to the invention. The control device can have a data processing device or a processor device which is set up to perform an embodiment of the method according to the invention. For this purpose, the processor device can have at least one microprocessor and/or at least one microcontroller and/or at least one FPGA (Field Programmable Gate Array) and/or at least one DSP (Digital Signal Processor). The processor device can also comprise program code, which is designed, upon execution by the processor device, to perform the embodiment of the method according to the invention. The program code can be stored in a data memory of the processor device. A processor circuit of the processor device can have, for example, at least one circuit board and/or at least one SoC (System on Chip).

The invention also includes further developments of the method according to the invention, which have features as already described in the context of the further developments of the measuring arrangement according to the invention and the energy storage arrangement according to the invention. For this reason, the corresponding developments of the method according to the invention are not described again here.

The motor vehicle according to the invention is preferably designed as an automobile, in particular as a passenger car or truck, or as a passenger bus or motorcycle.

The invention also comprises the combinations of the features of the described embodiments. The invention therefore also includes implementations that each have a combination of the features of several of the described embodiments, provided that the embodiments have not been described as mutually exclusive.

BRIEF DESCRIPTION OF THE FIGURES

Exemplary embodiments of the invention are described hereinafter. In particular.

DETAILED DESCRIPTION

The exemplary embodiments explained hereinafter are preferred embodiments of the invention. In the exemplary embodiments, the described components of the embodiments each represent individual features of the invention to be considered independently of one another, which each also develop the invention independently of one another. Therefore, the disclosure is also intended to comprise combinations of the features of the embodiments other than those represented. Furthermore, the described embodiments can also be supplemented by further ones of the above-described features of the invention.

Figure 1:
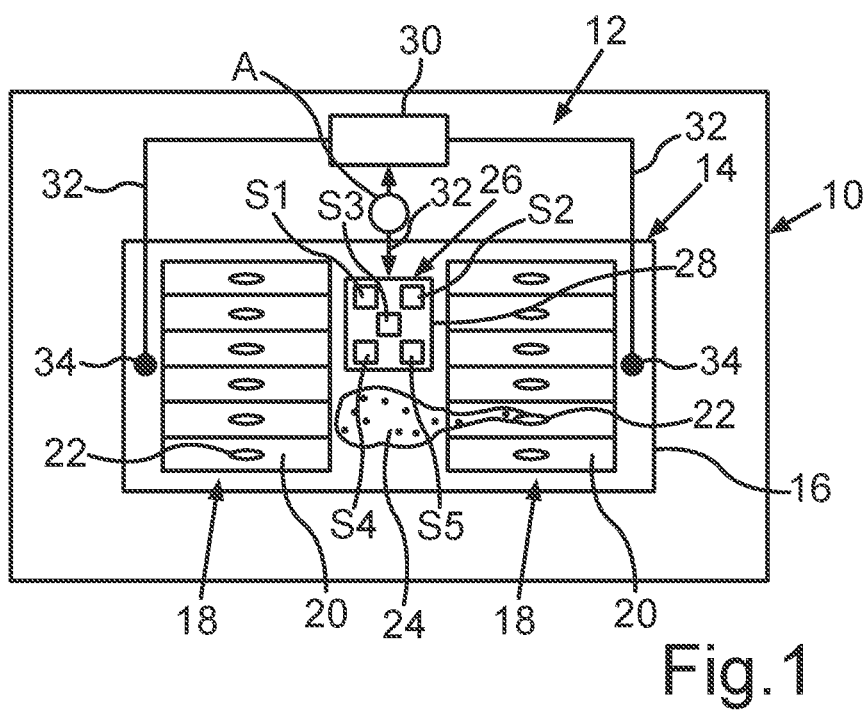
FIG. 1 shows a schematic illustration of a motor vehicle having an energy storage and a measuring arrangement according to an exemplary embodiment of the invention.

In the figures, same reference numerals respectively designate elements that have the same function FIG. 1 shows a schematic illustration of a motor vehicle 10 having a measuring arrangement 12 according to an exemplary embodiment of the invention. In addition to the measuring arrangement 12, the motor vehicle 10 has an energy storage 14, which is designed as a high-voltage energy storage, in particular as a high-voltage battery 14. The energy storage 14 has a battery housing 16, in which several battery modules 18, each with several battery cells 20, are arranged. For reasons of clarity, only one battery cell 20 per battery module 18 is provided with a reference number. Each of the battery cells 20 can have a releasable cell degassing opening 22. Here too, only some cell degassing openings 22 for some of the battery cells 20 are provided with a reference number. These releasable cell degassing openings 22 can be designed, for example, as bursting membranes. These are designed accordingly to burst at a certain excess pressure within the corresponding battery cell 20 and thereby enable outgassing of the corresponding cell 20. In the present example, a gas 24 emerging from a battery cell 20 is shown as an example. If gas 24 escapes from a battery cell 20 or from the energy storage 14, a fire is very likely. It is therefore very advantageous to detect such a gas leak as early as possible. For this purpose, the motor vehicle 10 has the measuring arrangement 12 already mentioned. This includes a thermal runaway sensor 26, which is also referred to as a gas sensor unit 26 in the context of the present invention.

The thermal runaway sensor 26 can generally be designed to measure escaping gases from the battery 14 and, if they occur, to warn the driver and/or to activate countermeasures, for example cooling the energy storage 14. A thermal runaway sensor, such as the sensor 26 described, measures, for example, gases escaping from the battery 14, when the latter becomes too hot.

This thermal runaway sensor 26 can in turn have one or more individual sensors S1, S2, S3, S4, S5. These individual sensors S1, S2, S3, S4, S5 can be designed to record different measured variables. These preferably represent H2, Co, ammonia, temperature and pressure. It is also conceivable that the thermal runaway sensor 26 has fewer than the five sensors mentioned, wherein the thermal runaway sensor 26 preferably comprises at least three of the sensors mentioned or is designed to detect at least three of the measured variables mentioned. This makes it possible to detect very reliably when gas 24 escapes from a cell 20 or from the entire battery 14. The thermal runaway sensor 26 is accordingly preferably arranged at a location within the motor vehicle 10 with respect to the energy storage 14, at which it can come into direct contact with the gas 24 emerging from a cell 20. The thermal runaway sensor 26 can also be arranged inside the battery housing 16, or outside and, for example, within a gas discharge channel for discharging the gas emerging from a cell 20 from the energy storage 14 and from the motor vehicle 10. The sensors S1, S2, S3, S4, S5 included in the thermal runaway sensor 26 are also preferably arranged in a common housing 28 of the thermal runaway sensor 26.

Furthermore, the measuring arrangement 12 in the present case comprises a control device 30. This is communicatively connected to the thermal runaway sensor 26. The connection can take place via a BUS system 32, for example a CAN-BUS. In addition, in the present example, further sensors, in particular temperature sensors 34, are arranged in the energy storage 14, in particular in the storage housing 16. These are designed to detect a temperature within the energy storage 14. The detected sensor signals from these temperature sensors 34 can also be transmitted to the control device 30 for evaluation, in particular also via the CANBUS 32. However, these temperature sensors 34 can also be connected to the control device 30 in another way. For example, if the thermal runaway sensor 26 detects that gas is emerging from a cell 20 or from the entire energy storage 14, it can communicate this to the control device 30. This can initiate a specific countermeasure, for example activating a cooling device for cooling the energy storage 14. In this way, for example, thermal runaway of all battery cells 20 can be counteracted and a battery fire can at least be delayed or even completely prevented. By providing such a thermal runaway sensor 26, safety can be increased.

Such a thermal runaway sensor 26 is usually in a permanently wake state. This means that the sensor is permanently switched on and continuously carries out measurements. It constantly requires energy and the overall lifespan is affected by this. The invention or its embodiments can advantageously avoid or reduce unnecessary energy consumption and also reduce the risk of damage or defects to the sensor during the vehicle's service life due to the continuous load described. A defect in such a thermal runaway sensor would require a complicated replacement in the battery module.

The present thermal runaway sensor 26 is connected via a system that supports a wake-up function. This can be a CAN BUS 32, but another BUS system or a wireless solution is also conceivable in order to implement the wake-up functionality of the gas sensor 26 or the gas sensor unit 26. It is therefore advantageously possible to only wake up the sensor assembly provided by the gas sensor unit 26 when this is necessary. It may be necessary, for example, by definition, if, for example, a time interval, for example five minutes, has expired or the battery management system or the control device 30, which can be part of such a battery management system, detects, via the temperature sensors 34 mentioned, which are provided, for example, as NTC sensors, an increase in temperature at cell contact. In other words, the temperature sensors 34 can be positioned in the region of cell contact, for example in the region of the cell connectors for electrically conductive connection of the cell poles.

In general, the control device 30 can be designed to transmit a wake-up signal A to the thermal runaway sensor 26 via the BUS system 32 or another communicative connection and thereby wake it up. In the wake state, the thermal runaway sensor 26 can correspondingly carry out a measurement and then, for example if there are no abnormalities, return to the inactive idle state, in particular until the next wake-up by the control device 30. The thermal runaway sensor 26, however, can also be designed with its own wake-up function, that is, it can activate itself at regular intervals in order to carry out a measurement without such a wake-up signal A having to be provided by the external control device 30.

In addition, it is also possible to control the different measuring ranges of the sensor 26 individually via the CAN BUS 32. In other words, not all sensors S1, S2, S3, S4, S5 of the gas sensor unit 26 have to be woken up at the same time, but they can also be woken up at different times from one another or according to different criteria. The wake-up functionality can therefore relate to the thermal runaway sensor 26 as a whole, or to each of its sensors S1, S2, S3, S4, S5 individually.

Different wake-up strategies and options are explained below with reference to FIGS. 2 and 3.

Figure 2:
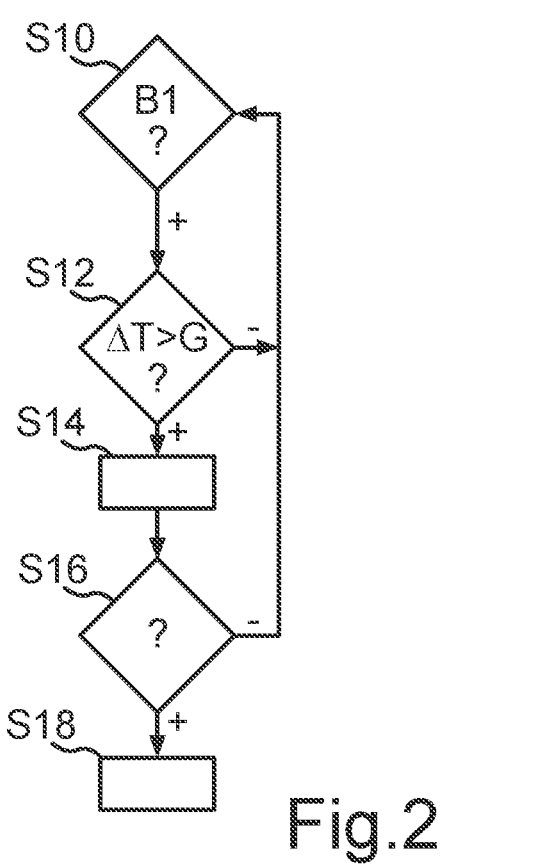
FIG. 2 shows a flowchart to illustrate a method for operating a measuring arrangement according to an exemplary embodiment of the invention.

FIG. 2 shows a flowchart to illustrate a method for operating a measuring arrangement 12 according to an exemplary embodiment of the invention. It is first checked in step S10 whether the gas sensor unit 26, that is to say the thermal runaway sensor 26, is in a first operating state B1. This step is purely optional. For example, this first operating state B1 can also be the only operating state in which the thermal runaway sensor 26 can be operated. However, it can also be provided that this wake-up functionality is only used in certain operating states, for example in operating states of the motor vehicle in which thermal runaway of the energy storage 14 is less likely. For example, the thermal runaway sensor 26 can only be put into this wake-up mode, which is different from the permanent wake state and is provided by this first operating state B1, when the motor vehicle 10 is not being charged and while the motor vehicle 10 or the energy storage 14 is charged by a vehicle-external energy source, the gas sensor 26 can, for example, be transferred to a permanent wake state in which it permanently carries out measurements.

In this first operating state B1, the thermal runaway sensor 26 is basically in an inactive idle mode and is not operated in a permanent wake state. Nevertheless, the thermal runaway sensor 26 is woken up every now and then to carry out a measurement. In the present example, it is first checked in step S12 whether a temperature increase $\Delta T$ is greater than a predetermined limit value G. This can be checked on the basis of the temperature of the energy storage 14 detected by the temperature sensors 34. If this is not the case, the process goes to step S10. In particular, these steps can be repeated until it is detected in step S12 that a predetermined large temperature increase $\Delta T$, for example based on a predetermined standard time interval, has been recorded. Subsequently, in step S14, the thermal runaway sensor 26 including all of its sensors S1 to S5 can be woken up, which sensors then accordingly carry out one or more measurements. It is then checked in step S16, in particular based on the measurement results supplied by the thermal runaway sensor 26, for example by the control device 30, whether an incipient thermal runaway is present. If this is not the case, the method goes back to step S10. Otherwise, a specific countermeasure can be initiated in step S16, for example cooling of the energy storage 14 can be activated. This can in turn be triggered by the control device 20.

Figure 3:
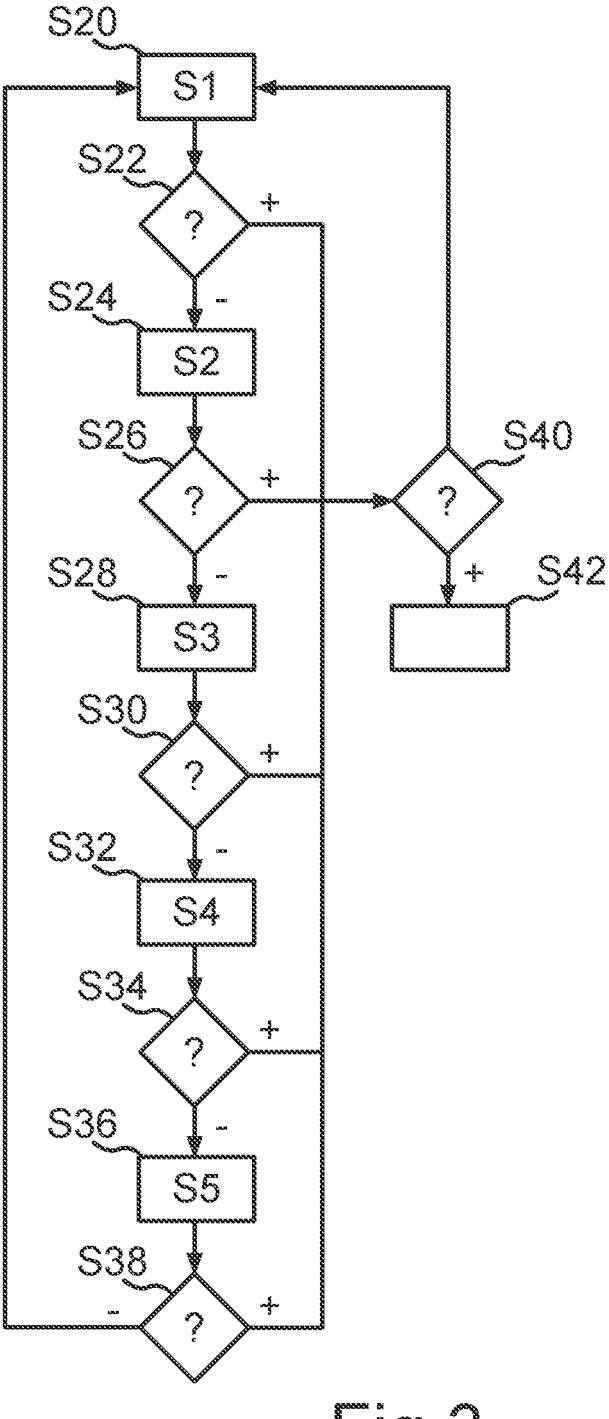
FIG. 3 shows a flowchart to illustrate a method for operating a measuring arrangement according to a further exemplary embodiment of the invention.

FIG. 3 shows a schematic representation of a flowchart to illustrate a method for operating a measuring arrangement 12 according to an exemplary embodiment of the invention. The method begins in step S20, in which in the present case only the first sensor S1 of the thermal runaway sensor 26 is woken up from the inactive idle state in order to carry out a measurement. If a measurement was carried out by this sensor S1, then in step S22 it is checked, in particular based on the measurement result provided by the first sensor S1, whether there is a specific abnormality that makes a thermal runaway of a battery cell 20 appear possible or probable. If this is not the case, the first sensor S1 is put back into the inactive idle state. After a predetermined period of time has elapsed after the activation of the first sensor S1, the second sensor S2 is woken up from the inactive idle state and a measurement is carried out by it in step S24. Based on the measurement result, it is again checked in step S26 whether there is a specific abnormality that makes a thermal event appear possible or probable. If this is not the case, the second sensor S2 is put back into the idle state and after a predetermined period of time has elapsed in step S28 the third sensor S3 is woken up and a corresponding measurement is carried out using it. Subsequently, in step S30 it is checked again whether a certain abnormality is present and if this is not the case, the third sensor S3 is put back into the idle state. After a certain period of time has elapsed, the fourth sensor is woken up in step S32 and a measurement is carried out using this fourth sensor S4. In step S34 it is again checked whether there is a specific abnormality based on the measurement result provided by the fourth sensor S4. If this is not the case, the fourth sensor S4 is put back into the idle state and after a predetermined period of time the fifth sensor S5 is woken up in step S36 and a measurement is carried out with it. In step S38 it is checked whether the measurement result of the fifth sensor S5 provides a specific abnormality. If this is not the case, it goes back to step S20, in particular again after a certain period of time has elapsed. This can always be the same period of time or it can be different periods of time. As a simple example, from a starting point after minute 1, the first sensor S1 can be woken up to carry out a hydrogen measurement, after minute 2 the second sensor S2 can be woken up to carry out a CO measurement, and after minute 3 the pressure sensor S3 can be woken up to carry out a pressure measurement, after minute 4 the temperature sensor S4 can be woken up to measure the current temperature, after minute 5 the ammonia sensor S5 can be woken up to carry out an ammonia measurement, after minute 6 the hydrogen sensor S1 can be woken up again to perform another hydrogen measurement, after minute 7 the CO sensor can be woken up again to carry out a CO measurement, and so on. The respective sensors are immediately put back into the idle state after their respective measurements have been carried out. In this example, a relevant sensor is only woken up every five minutes. Overall, however, a measurement can be carried out every minute. This therefore provides a very high measurement frequency. Overall, however, each individual sensor is only woken up very rarely. This allows further savings in electricity consumption. Each of the sensors S1 to S5 can therefore be controlled separately. This results in a wide range of possibilities overall. Furthermore, certain abnormalities can be monitored specifically using the appropriate factor. Relevant monitoring variables, for example the ammonia concentration or the CO concentration, can be measured more frequently than others.

If an abnormality is detected in any measurement, in particular in one of the checking steps S22, S26, S30, S34 and/or S38, the process can, for example, go to step S40, in which one or more control measurements are performed, for example, by all of the sensors S1 to S5 of the thermal runaway sensor 26. Based on such a new control measurement, it can be checked in step S40 whether a thermal runaway of a cell 20 is present. If this is the case, a cooling device can again be activated in step S42 or another countermeasure can be initiated. Otherwise, the process can go back to step S20.

Overall, this makes it possible for the thermal runaway sensor 26 to be operated with significantly lower energy consumption. In addition, its lifespan can be increased. In addition, new possibilities for precise measurements arise. To implement this, the thermal runaway sensor 26 can simply be connected to a wake-up capable communication system and a suitable wake-up moment can be defined.

Overall, the examples show how the invention can provide the use of a thermal runaway sensor in a vehicle in an operating mode which is part of a wake-up function.

The invention claimed is:

1. A measuring arrangement for gas monitoring for an energy storage of a motor vehicle, comprising: at least one battery cell, wherein the measuring arrangement has a gas sensor unit which comprises at least one first sensor, wherein the gas sensor unit is designed to detect a gas leak from the at least one battery cell, wherein the measuring arrangement is designed in such a way that at least in a first operating state of the gas sensor unit, at least the first sensor can be woken up from an inactive idle state for carrying out at least one measurement and can be put back into the inactive idle state after the at least one measurement has been carried out, wherein the gas sensor unit comprises a plurality of sensors including the first sensor and at least one second sensor, wherein the measuring arrangement is designed such that at least the first sensor is woken up repeatedly in the first operating state of the gas sensor unit, at predetermined first time intervals, in order to carry out a measurement, and wherein the measuring arrangement is designed such that, in a second operating state of the gas sensor unit, the at least one second sensor is woken up repeatedly at predetermined second time intervals to carry out a measurement, the predetermined second time intervals being different from the predetermined first time intervals.

2. The measuring arrangement according to claim 1, wherein the measuring arrangement is designed such that at least the first sensor is woken up in the first operating state of the gas sensor unit in response to a wake-up signal, in order to carry out the measurement.

3. The measuring arrangement according to claim 2, wherein the measuring arrangement has a control device which is designed to wake up at least the first sensor in the first operating state of the gas sensor unit, and to provide the wake-up signal depending on the detection of a specific event, wherein the specific event represents a predetermined temperature increase detected by a temperature sensor of the measuring arrangement, and/or represents an exceeding of a predetermined limit temperature detected by a temperature sensor of the measuring arrangement; and/or represents an accident detected by a crash sensor of the measuring arrangement, and/or represents a specific characteristic of a current or a voltage of the at least one battery cell and/or energy storage, detected by means of a current and/or voltage sensor.

4. The measuring arrangement according to claim 2, wherein the gas sensor unit has several different sensors comprising the first sensor, which are designed to detect at least one of the following events and/or variables:

an occurrence of a carbon oxide and/or a concentration of a carbon oxide;

an occurrence of hydrogen and/or a concentration of hydrogen;

an occurrence of ammonia and/or a concentration of ammonia;

a temperature; and a gas pressure.

5. The measuring arrangement according to claim 2, wherein the measuring arrangement is designed such that, at least in the first operating state of the gas sensor unit, all of the sensors included in the gas sensor unit can be woken up from an inactive idle state in order to carry out at least one respective measurement simultaneously, and after carrying out the respective at least one measurement can be put back into the inactive idle state simultaneously.

6. The measuring arrangement according to claim 1, wherein the measuring arrangement has a control device which is designed to wake up at least the first sensor in the first operating state of the gas sensor unit, and to provide a wake-up signal depending on the detection of a specific event, wherein the specific event represents a predetermined temperature increase detected by a temperature sensor of the measuring arrangement, and/or represents an exceeding of a predetermined limit temperature detected by a temperature sensor of the measuring arrangement; and/or represents an accident detected by a crash sensor of the measuring arrangement, and/or represents a specific characteristic of a current or a voltage of the at least one battery cell and/or energy storage, detected by means of a current and/or voltage sensor.

7. The measuring arrangement according to claim 6, wherein the gas sensor unit has several different sensors comprising the first sensor, which are designed to detect at least one of the following events and/or variables:

an occurrence of a carbon oxide and/or a concentration of a carbon oxide;

an occurrence of hydrogen and/or a concentration of hydrogen;

an occurrence of ammonia and/or a concentration of ammonia;

a temperature; and a gas pressure.

8. The measuring arrangement according to claim 6, wherein the measuring arrangement is designed such that, at least in the first operating state of the gas sensor unit, all of the sensors included in the gas sensor unit can be woken up from an inactive idle state in order to carry out at least one respective measurement simultaneously, and after carrying out the respective at least one measurement can be put back into the inactive idle state simultaneously.

9. The measuring arrangement according to claim 1, wherein the gas sensor unit has several different sensors comprising the first sensor, which are designed to detect at least one of the following events and/or variables:

an occurrence of a carbon oxide and/or a concentration of a carbon oxide;

an occurrence of hydrogen and/or a concentration of hydrogen;

an occurrence of ammonia and/or a concentration of ammonia;

a temperature; and a gas pressure.

10. The measuring arrangement according to claim 9, wherein the measuring arrangement is designed such that, at least in the first operating state of the gas sensor unit, all of the sensors included in the gas sensor unit can be woken up from an inactive idle state in order to carry out at least one respective measurement simultaneously, and after carrying out the respective at least one measurement can be put back into the inactive idle state simultaneously.

11. The measuring arrangement according to claim 1, wherein the measuring arrangement is designed such that, at least in the first operating state of the gas sensor unit, all of the sensors included in the gas sensor unit can be woken up from an inactive idle state in order to carry out at least one respective measurement simultaneously, and after carrying out the respective at least one measurement can be put back into the inactive idle state simultaneously.

12. The measuring arrangement according to claim 1, wherein the measuring arrangement is designed such that, at least in the first operating state of the gas sensor unit, all sensors included in the gas sensor unit can be woken up to carry out at least one respective measurement from an inactive idle state, (i) according to different, specified criteria and/or (ii) independently of each other.

13. The measuring arrangement according to claim 1, wherein, in the second operating state of the gas sensor unit, the first and second sensors are woken up at least partially with a time offset from one another.

14. An energy storage arrangement with an energy storage for a motor vehicle and with a measuring arrangement according to claim 1.

15. A method for operating a measuring arrangement for gas monitoring for an energy storage of a motor vehicle, which comprises at least one battery cell, wherein the measuring arrangement has a gas sensor unit which comprises at least one first sensor, wherein the gas sensor unit is designed to detect a gas leak from the at least one battery cell, wherein at least in a first operating state of the gas sensor unit, at least the first sensor is woken up from an inactive idle state for carrying out at least one measurement and is put back into the inactive idle state after the at least one measurement has been carried out, wherein the gas sensor unit comprises a plurality of sensors including the first sensor and at least one second sensor, wherein the measuring arrangement is designed such that at least the first sensor is woken up repeatedly in the first operating state of the gas sensor unit, at predetermined first time intervals, in order to carry out a measurement, and

wherein the measuring arrangement is designed such that, in a second operating state of the gas sensor unit, the at least one second sensor is woken up repeatedly at predetermined second time intervals to carry out a measurement, the predetermined second time intervals being different from the predetermined first time intervals.

\* \* \* \* \*